(12) United States Patent
Robinson

(10) Patent No.: US 9,198,688 B2
(45) Date of Patent: Dec. 1, 2015

(54) BIOPSY GUIDE WITH AN ULTRASOUND TRANSDUCER AND METHOD OF USING SAME

(75) Inventor: Andrew Lee Robinson, Bellevue, WA (US)

(73) Assignee: Koninklijke Philips N.V., Eindhoven (NL)

( * ) Notice: Subject to any disclaimer, the term of this patent is extended or adjusted under 35 U.S.C. 154(b) by 143 days.

(21) Appl. No.: 13/266,795

(22) PCT Filed: Apr. 23, 2010

(86) PCT No.: PCT/IB2010/051782
§ 371 (c)(1),
(2), (4) Date: Oct. 28, 2011

(87) PCT Pub. No.: WO2010/125505
PCT Pub. Date: Nov. 4, 2010

(65) Prior Publication Data
US 2012/0059260 A1 Mar. 8, 2012

Related U.S. Application Data

(60) Provisional application No. 61/173,285, filed on Apr. 28, 2009.

(51) Int. Cl.
*A61B 10/02* (2006.01)
*A61B 8/14* (2006.01)
*A61B 17/34* (2006.01)
(Continued)

(52) U.S. Cl.
CPC ............ *A61B 17/3403* (2013.01); *A61B 8/0841* (2013.01); *A61B 8/483* (2013.01); *G01S 7/52073* (2013.01); *G01S 7/52074* (2013.01);
(Continued)

(58) Field of Classification Search
CPC .... A61B 8/0841; A61B 8/483; A61B 8/0833; A61B 17/3403; A61B 2017/3413; G01S 7/52073; G01S 7/52074; G01S 15/8993
USPC .......................................................... 600/461
See application file for complete search history.

(56) References Cited

U.S. PATENT DOCUMENTS 4,608,989 A * 9/1986 Drue ............................ 600/461
4,870,867 A * 10/1989 Shaulov ....................... 600/461
(Continued)

FOREIGN PATENT DOCUMENTS

EP   0955010       10/1999
EP   1323380 A2    7/2003
(Continued)

*Primary Examiner* — Long V Le
*Assistant Examiner* — Colin T Sakamoto

(57) ABSTRACT

A multi-position biopsy guide system and a method of using such biopsy guide system is proposed. The biopsy guide system comprises a 2D matrix ultrasound transducer (3) and comprises at least one biopsy needle guide (5) adapted for guiding a biopsy needle along a biopsy path (7). Therein, the multi-position biopsy guide system is adapted to controllably guide the biopsy needle along biopsy paths at variable locations with respect to the 2D matrix ultrasound transducer. Preferably, a location of the biopsy needle guide (5) with respect to the matrix ultrasound transducer may be determined and an ultrasound image in an image plane aligned with a biopsy path corresponding to the determined location of the biopsy needle guide may be acquired. Thereby, a biopsy process may be monitored for various locations and orientations of a guided biopsy needle.

14 Claims, 3 Drawing Sheets

(51) Int. Cl.
*G01S 7/52* (2006.01)
*A61B 8/08* (2006.01)
*G01S 15/89* (2006.01)

(52) U.S. Cl.
CPC ....... *A61B8/0833* (2013.01); *A61B 2017/3413* (2013.01); *G01S 15/8993* (2013.01)

(56) References Cited

U.S. PATENT DOCUMENTS

| | | | |
|---|---|---|---|
| 6,336,899 B1 * | 1/2002 | Yamazaki | 600/461 |
| 6,361,499 B1 | 3/2002 | Bates et al. | |
| 6,485,426 B2 * | 11/2002 | Sandhu | 600/461 |
| 6,546,279 B1 * | 4/2003 | Bova et al. | 600/429 |
| 6,695,786 B2 * | 2/2004 | Wang et al. | 600/461 |
| 6,733,458 B1 * | 5/2004 | Steins et al. | 600/461 |
| 8,574,160 B2 * | 11/2013 | Gorzitze | 600/461 |
| 2002/0156376 A1 | 10/2002 | Wang et al. | |
| 2002/0173719 A1 | 11/2002 | Zhao et al. | |
| 2005/0059891 A1 * | 3/2005 | Kosaku | 600/459 |
| 2007/0112272 A1 * | 5/2007 | Park et al. | 600/461 |
| 2007/0167769 A1 * | 7/2007 | Ikuma et al. | 600/437 |
| 2009/0143684 A1 * | 6/2009 | Cermak et al. | 600/461 |
| 2009/0171219 A1 * | 7/2009 | Uchibori | 600/461 |

FOREIGN PATENT DOCUMENTS

| | | |
|---|---|---|
| EP | 1804079 A2 | 7/2007 |
| JP | 078497 A | 1/1995 |
| JP | 2002102221 | 4/2002 |
| JP | 2007175431 | 7/2007 |
| WO | 2006060657 | 6/2006 |
| WO | 2006/109219 A1 | 10/2006 |
| WO | 2007/027511 A2 | 3/2007 |
| WO | 2007110076 | 10/2007 |

\* cited by examiner

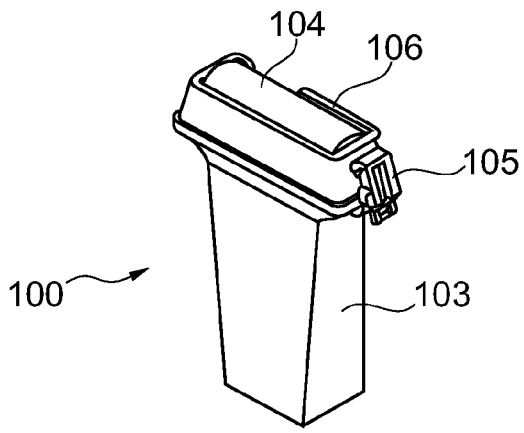
Fig. 1
(prior art)
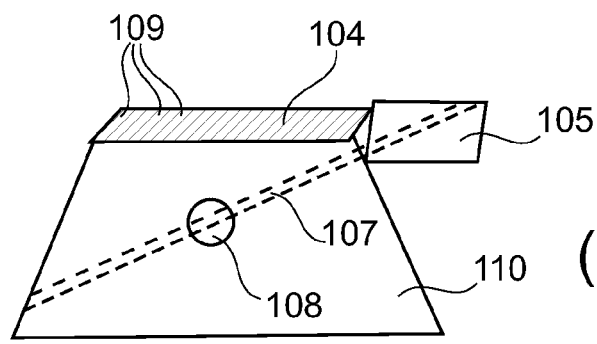
Fig. 2
(prior art)
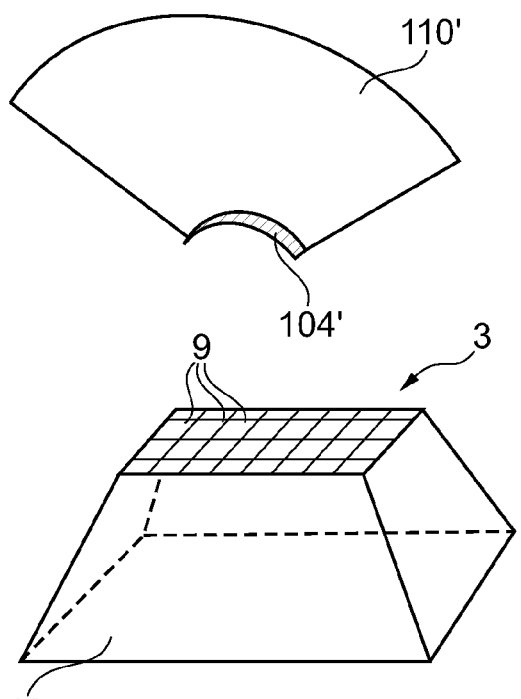
Fig. 3
(prior art)
Fig. 4

BIOPSY GUIDE WITH AN ULTRASOUND TRANSDUCER AND METHOD OF USING SAME

This application claims the priority of international application no. PCT/IB2010/051782, filed Apr. 23, 2010, which claims the benefit of U.S. provisional application Ser. No. 61/173,285, filed Apr. 28, 2009.

FIELD OF THE INVENTION

The invention relates to a biopsy guide system for guiding a biopsy needle along a biopsy path while monitoring with an ultrasound transducer. Furthermore, the invention relates to a method of controlling guidance of a biopsy needle using such biopsy guide.

BACKGROUND OF THE INVENTION

A biopsy is a medical test involving the removal of cells or tissues from a region of interest such as a lesion for medical examination purposes. The removed cells or tissues may be examined in order to detect the presence or extent of a disease.

For removing the cells or tissues, a biopsy needle has to be introduced into a patient's body and has to be guided to the region of interest. In order to enable monitoring of the introduction and guidance of the biopsy needle, ultrasound transducers are frequently used to observe the region of interest during the insertion of the biopsy needle.

As described for example in WO2006/060657-A2, a biopsy needle guide adapted for guiding a biopsy needle along a biopsy path may be coupled to a conventional ultrasound transducer device.

As schematically shown in FIGS. 1-3, a conventional ultrasound transducer 103 comprises a one-dimensional (1D) transducer face 104 from which ultrasonic signals may be emitted. Thereby, an image plane underneath the transducer face may be observed by detecting echoes of reflected ultrasonic signals coming from inhomogeneities of the observed region. By correctly positioning the ultrasound transducer 103, a region of interest comprising for example a lesion 108 may be observed. A biopsy needle guide 105 may be attached close to the transducer face 104 and may be adapted to guide a biopsy needle along a biopsy path 107 into the lesion 108.

Conventional one-dimensional ultrasound transducers comprise an array of elements 109 arranged in a line. A division of elements 109 in a line allows each element 109 to transmit and receive separate ultrasound signals, which may be combined to generate an image. The transducers array face 104 is usually a rectangle, where the long direction is generally referred to as the "azimuth" direction and the orthogonal direction is generally referred to as the "elevation" direction. Because the elements 109 are arranged in a single line, the ultrasound beam can be steered and focused in a region that is orthogonal to the face 104 of the transducer 103 but which is most simply described as a plane. This plane extends in the azimuth direction and in the "range" direction, where the range direction is orthogonal to the transducer array face and therefore orthogonal to both the azimuth and elevation directions. Although the transducer face is usually a rectangle, the field of view may be a triangle, rectangle or trapezoid that is orthogonal to the array face 104 and extends in the azimuth and range directions; this is generally referred to as the azimuthal plane.

In the example shown in FIG. 2, the field of view 110 is trapezoidal. The length of the transducer array in the elevation direction may determine, in conjunction with a mechanical lens, the focal characteristics in the elevation direction generally referred to as "slice thickness". Ideally, slice thickness would be zero so that the image represents a cross-section of the patient orthogonal to the face of the array, but in practice, slice thickness cannot be zero. The image presented on the ultrasound system screen, while portrayed in a single plane, is in fact a projection of the ultrasound information contained in the non-zero slice in the azimuth plane. The slice thickness is not constant throughout the depth of the image. At the face of the transducer, it is equal to the elevation direction; as depth increases the slice thickness decreases as the elevation direction and lens curvature are combined to focus the ultrasound energy; past the focal depth, i.e. the depth at which the slice thickness is smallest, the ultrasound beam diverges and the slice thickness increases. To further complicate matters, the ultrasound beam does not have perfectly sharp boundaries. In the below description, simple planar structures will be used to illustrate ultrasound imaging fields of view that are in fact a fairly complex sampling of a three-dimensional space.

While in FIG. 1, the ultrasound transducer 103 is shown with a planar one-dimensional array face 104, the one-dimensional array can also be formed on a curved surface, in which case it is generally referred to as a "curved linear array" (CLA). This is illustrated in FIG. 3. Such a CLA, rather than being a rectangle, is a section of a cylinder. The resulting field of view 110' is a section of a circle with the inner boundary being the array face 104'. Although, in the following description, most of the examples presented are for a flat array, the ideas of the invention may be equally applicable to a curved array.

As in conventional biopsy guide systems the ultrasound transducer acquires an image of the observed tissue only along an azimuthal plane, the biopsy needle guide attached to the ultrasound transducer is usually designed to support needle entry on the azimuthal plane. A different needle guide location could be used, but since the biopsy needles path would not fall within the single available imaging plane, no guidance imaging may be available as the needle will not be visible until it passes through the imaging plane.

Accordingly, in conventional biopsy procedures, the biopsy guide system including the ultrasound transducer will be moved along the surface above the region of interest until the actual region of interest (including e.g. a lesion) may be seen on the acquired ultrasound image, i.e. until the imaging plane crosses the region of interest. Then, the biopsy needle may be introduced into the tissue along the azimuthal plane. As the needle moves along the imaging plane, the current location of the needle may be monitored in the ultrasound image. A biopsy may be taken as soon as the region of interest has been reached.

SUMMARY OF THE INVENTION

The inventor has considered that a desirable point of entry for the biopsy needle may be constrained by acoustic access or other features on the patient's body. Therefore, it may be desirable to be able to image needle entry from another position. For example, it may be desirable to image the entry of a needle introduced from a position different to the azimuthal position.

It is an object of the invention to provide a biopsy guide system which allows for an improved flexibility in selecting an entry location for a biopsy needle while enabling monitoring an insertion of the biopsy needle. It is another object of the invention to provide a method of controlling the guidance of a biopsy needle using such biopsy guide system.

The invention is defined by the independent claims. Advantageous embodiments are defined in the dependent claims.

According to a first aspect of the present invention, a multi-position biopsy guide system is proposed. It comprises a 2D matrix ultrasound transducer and at least one biopsy needle guide adapted for guiding a biopsy needle along a biopsy path. Therein, the multi-position biopsy guide system is adapted to controllably guide the biopsy needle along biopsy paths at variable locations with respect to the 2D matrix ultrasound transducer.

According to a second aspect of the present invention, a method of controlling guidance of a biopsy needle along a biopsy path using the multi-position biopsy guide system according to the first aspect of the invention is proposed. The method comprises (a) determining a location of the biopsy needle guide with respect to the 2D matrix ultrasound transducer, and (b) acquiring an ultrasound image in an image plane aligned with a biopsy path corresponding to the determined location of the biopsy needle guide.

The present invention may be seen as based on the following idea:

In conventional biopsy guide systems using one-dimensional ultrasound transducer arrays, a biopsy needle has to be guided such that it enters into the tissue in alignment with the imaging plane of the ultrasound transducer. Accordingly, only biopsy needles introduced along a biopsy path correctly aligned may be monitored.

The multi-position biopsy guide system according to the first aspect of the present invention comprises a two-dimensional matrix ultrasound transducer. Such transducer may comprise an array of ultrasound transducer elements arranged in columns and rows. The transducer array face may still be rectangular as in the case of a one-dimensional ultrasound transducer but the array of transducer elements is separated into a two-dimensional matrix. This additional complexity may allow for ultrasound beams to be steered and focused through a three-dimensional space rather than in only a nominal plane.

Thus, the field of view, rather than being a single trapezoid, may be a volume that is generally a truncated pyramid or, in the case of a sector transducer, an entire pyramid with its apex at the transducer face. Information from within the field of view may be acquired and displayed in many ways. The user may choose to view one or more planes in an azimuth or elevation direction. It is also possible to illustrate so-called X-plane imaging, where an azimuth and an elevation plane are displayed simultaneously. Furthermore, diagonal planes may be imaged. Finally, ultrasound information can be rendered into a 3D or volume representation, the best known example of which is the so-called "baby face". This list of potential display planes may not be complete but illustrates the capability of matrix transducers to display information acquired from within the volume field of view.

An idea of the present invention is to exploit this capability of flexible image acquisition and display from within the volume field of view. Using a 2D matrix ultrasound transducer enables alignment of an image plane with an arbitrary biopsy path along which a biopsy needle is guided into a patient's tissue. Accordingly, a biopsy needle guide may be arranged at any desired location for example along a circumference of the matrix ultrasound transducer and the ultrasound transducer may be controlled such as to acquire an ultrasound image in an imaging plane coinciding with a biopsy path along which a biopsy needle is guided by the biopsy needle guide.

Accordingly, the proposed biopsy guide system that provides for multiple needle entry locations would allow a user to choose the most appropriate location for a given situation. Multiple needle entry locations may take advantage of imaging capabilities of a matrix transducer, in particular the ability to image multiple planes simultaneously or alternatively (e.g. X-planes), planes that do not align to the transducers primary axis (azimuth or elevation), or volumes.

In accordance with specific embodiments of the present invention described further below in more detail, it is also possible to adapt the location and/or orientation of an imaging plane to a varying location of a biopsy needle for example in a case, where a flexible biopsy needle is deflected from its originally intended biopsy path due to inhomogeneities in the patient's tissue or due to other mechanical obstacles. Furthermore, it is also possible to monitor the insertion of two or more biopsy needles introduced simultaneously or alternately along different biopsy paths.

Possible features and advantages of embodiments of the present invention will be described in more detail in the following.

The two-dimensional matrix ultrasound transducer used in the proposed multi-position biopsy guide system may comprise a multiplicity of ultrasound transceiver elements adapted for emitting ultrasound waves and receiving echoes thereof. The elements may be arranged in a matrix fashion such that each row and each column comprises a plurality of adjacent transducer elements. The size of each transducer element as well as the overall size and geometry of the matrix ultrasound transducer may be adapted to a specific application. For example, the matrix ultrasound transducer may comprise a rectangular array of transducer elements. The transducer elements may be arranged and controlled such as to enable steering and focusing of an emitted ultrasound wave in any arbitrary direction or plane within a three-dimensional region of observation.

The biopsy needle guide of the proposed multi-position biopsy guide system may be adapted such that the biopsy needle may be introduced into a patient's tissue along a biopsy path wherein the location of the biopsy path may be controllably varied. For example, the biopsy needle guide may be either located in an azimuth position with respect to a rectangular 2D matrix ultrasound transducer or, alternatively, in an elevation position. It may also be positioned at any other location with respect to the ultrasound transducer. Alternatively, a multiplicity of biopsy needle guides may be arranged at different locations with respect to the ultrasound transducer such that each of the biopsy needle guides may introduce a biopsy needle along a different biopsy path.

According to an embodiment of the present invention, the two-dimensional matrix ultrasound transducer is adapted to acquire ultrasound images in an image plane which image plane is controllably variable. In other words, the ultrasound transducer may be controlled, e.g. by a control device, in a manner that addresses the transducer elements of the matrix transducer in such a way that ultrasound signals are emitted in a selectable imaging plane. From the detected echoes, an image of the region of observation in this imaging plane can be acquired.

According to another embodiment of the present invention, the multi-position biopsy guide system is adapted to mount the biopsy needle guide in variable locations with respect to the 2D matrix ultrasound transducer. In other words, one or more biopsy needle guides may be mounted at one of a plurality of possible mounting locations for example along a circumference around the matrix ultrasound transducer. Then, for example depending on space requirements occurring in a specific medical application, a biopsy needle may be guided along a preferred biopsy path using a biopsy needle guide located in one of the provided possible locations.

According to a further embodiment of the present invention, the multi-position biopsy guide system is adapted to determine the location of the biopsy needle guide with respect to the 2D matrix ultrasound transducer. For example, the location of the biopsy needle guide may be input manually by a user after previous mounting of the biopsy needle guide at a specific location. Alternatively, the proposed multi-position biopsy guide system may automatically determine the location of the biopsy needle guide. For example, switches may be provided at possible mounting locations for the biopsy needle guide such that, when a biopsy needle guide is mounted at a specific location, a respective switch is operated and indicates the location.

According to a further embodiment of the present invention, the multi-position biopsy guide system is adapted to acquire an ultrasound image in an image plane aligned with the biopsy path corresponding to the determined location of a biopsy needle guide. In other words, the proposed multi-position biopsy guide system may have a control device which is, on the one hand, able to determine the location of the biopsy needle guide and which, on the other hand, is able to control the 2D matrix ultrasound transducer such that an ultrasound image is acquired in an imaging plane which is aligned with the biopsy path of a biopsy needle guided by the biopsy needle guide in the determined location. Accordingly, ultrasound imaging may be automatically aligned with the biopsy path thereby allowing easy and fast monitoring of the process of introducing the biopsy needle.

According to a further embodiment of the present invention, the proposed multi-position biopsy guide system comprises at least two biopsy needle guides. In such embodiment, the two biopsy needle guides may be arranged such that biopsy needles may be introduced into a patient's tissue along biopsy paths extending in different planes. For example, one biopsy needle guide may be arranged in an azimuth direction and another biopsy needle guide may be arranged in an elevation direction. Alternatively, further biopsy needle guides may be provided for example in a diagonal direction. Each of the biopsy needle guides may be used alternatively depending on specific requirements of a medical application. For example, in one medical application, it may be advantageous to introduce a biopsy needle along an azimuthal direction whereas in another medical application the elevation direction may be preferred.

It may also be advantageous to use the at least two biopsy needle guides to introduce two or more biopsy needles simultaneously. For example, it may be desired to introduce a first biopsy needle to a region of interest for application of a medical, pharmaceutical or contrast agent. A second biopsy needle may be used to actually acquire a biopsy sample from the region of interest. Alternatively, two biopsy needles may be guided to a region of interest to apply therapy treatment in order to destroy deteriorated tissue.

According to a further embodiment of the present invention, the multi-position biopsy guide system is adapted to acquire ultrasound images in respective image planes aligned with the biopsy paths of each of the biopsy needle guides. In other words, as the 2D matrix ultrasound transducer may be able to acquire ultrasound images in any arbitrary image plane, it may be advantageous to acquire ultrasound image in imaging planes coinciding with each of the possible biopsy paths such that introduction of one or preferably several biopsy needles along the several possible biopsy paths may be observed quasi-simultaneously or alternately.

According to a further embodiment of the present invention, the biopsy needle guide is adapted for guiding the biopsy needle along a biopsy path at controllably variable angles. In other words, a biopsy needle guide may include provisions to allow for different tilting of a guided biopsy needle such that the biopsy needle may be introduced into a patient's tissue under a selectable angle. Accordingly, the introduction angle of the biopsy needle can be chosen such that a specific location of a region of interest may be reached with the biopsy needle. This may be particularly advantageous in case a biopsy needle guide may be mounted at the proposed multi-position biopsy guide system at different selected locations such as at azimuth locations or at elevation locations. Depending on the selected location, a different introduction angle may be required for the biopsy needle in order to reach a region of interest.

According to a further embodiment of the present invention, the biopsy needle guide is adapted for guiding different types of biopsy needles. The type of biopsy needle may be adapted for a specific medical application. For example, the biopsy needles may differ in length, shape or diameter.

According to a further embodiment of the present invention, the 2D matrix ultrasound transducer is adapted to acquire 3D ultrasound images. The ability of a 2D matrix ultrasound transducer to acquire ultrasound images from a volume may allow for the ability of deriving 3D ultrasound images. Thereby, it is possible to provide a 3D or volume representation of a region of interest. Such 3D representation may even be time-dependent (sometimes referred to as "live 3D" or "4D") by concatenating a plurality of 3D representations acquired in a time sequence. Biopsy needles may be guided within an acquired 3D image. Biopsy guidance in live 3D may provide better awareness of nearby structures and may thereby help to avoid mistakes during the procedure.

A biopsy arrangement comprising a multi-position biopsy guide system as described above and further comprising a display device for displaying ultrasound images acquired by the 2D matrix ultrasound transducer may be used to assist a physician in finding a region of interest and/or monitoring the guidance of a biopsy needle towards the region of interest. For example, an ultrasound image may be displayed on the display device wherein the location and orientation of the image plane in which the ultrasound image is acquired may be manually aligned by the surgeon or automatically aligned by the biopsy arrangement itself such that a process of introducing the biopsy needle may be effectively monitored. Alternatively, two or more ultrasound images may be acquired and displayed. For example, a first ultrasound image may be acquired in a direction coinciding with the biopsy path while a second ultrasound image may be acquired in a direction orthogonal thereto. From the second ultrasound image a surgeon may learn where the biopsy needle crosses the region of interest in a plane perpendicular to the biopsy path. Alternatively, two or more biopsy needles may be monitored. The two or more ultrasound images may be displayed simultaneously, for example side-by-side, or alternately. Accordingly, a surgeon may acquire image information and monitor a biopsy process in different imaging planes without the necessity to move the ultrasound transducer.

According to an embodiment of the method according to the above second aspect of the invention, at least two biopsy needles are guided using separate biopsy needle guides and each biopsy needle is visualized in respective corresponding imaging planes using the 2D matrix ultrasound transducer (3). Both needles may be visualized simultaneously or alternately.

It has to be noted that aspects and embodiments of the present invention have been described with reference to different subject-matters. In particular, some embodiments have been described with reference to apparatus-type claims whereas other embodiments or features have been described with reference to method-type claims. However, a person skilled in the art will gather from the above and the following description that, unless other notified, in addition to any combination of features belonging to one type of subject-matter also any combination between features relating to different subject-matters, in particular between features of the apparatus-type claims and features of the method-type claims, is considered to be disclosed with this application.

BRIEF DESCRIPTION OF THE DRAWINGS

Features and advantages of the present invention will be further described with respect to specific embodiments as shown in the accompanying figures but to which the invention shall not be limited.

FIG. 1 shows a perspective view of a conventional biopsy guide.

FIG. 2 shows a schematical side view of a conventional biopsy guide system with a one-dimensional ultrasound transducer.

FIG. 3 schematically shows a one-dimensional ultrasound transducer surface with a curved linear array (CLA).

FIG. 4 schematically shows a two-dimensional matrix ultrasound transducer usable in a multi-position biopsy guide system according to an embodiment of the present invention.

The drawings are only schematical and not to scale. Similar elements are indicated with similar reference signs.

DETAILED DESCRIPTION OF INVENTION

Figures 5A, 5B:
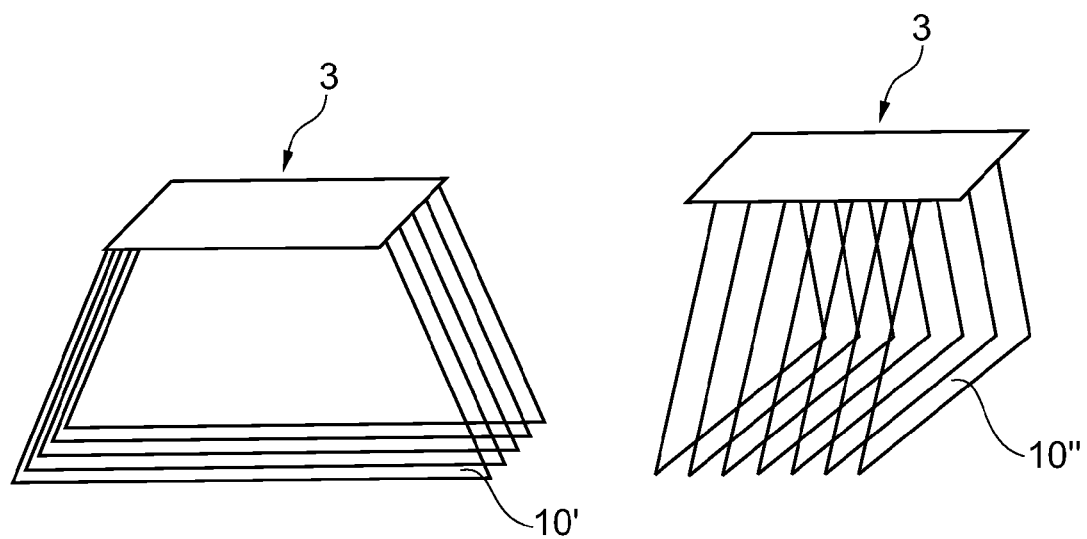
FIGS. 5a, 5b illustrate azimuthal and elevational oriented imaging planes of the two-dimensional matrix ultrasound transducer shown in FIG. 4.

The conventional biopsy guide system 100 shown in FIG. 1 comprises a 1D ultrasound transducer 103. A biopsy guide bracket 106 is arranged around the transducer face 104. In an azimuthal position with respect to the longitudinal transducer face 104, a biopsy needle guide 105 is attached to the biopsy guide bracket 106. As indicated in FIG. 2, the ultrasound transducer 103 with the one-dimensional transducer face 104 is adapted to acquire an image from within a trapezoidal region included in an image plane 110 coinciding with and orthogonal to the transducer face 104.

While with the conventional biopsy guide system shown in FIGS. 1 and 2 the image plane 110 has to be moved together with the biopsy guide system until it coincides with a region of interest 108 such that a biopsy needle may be guided along a biopsy path 107 using the biopsy needle guide 105, FIG. 4 illustrates an advantage which may be obtained when using a two-dimensional matrix ultrasound transducer for the biopsy guide system in accordance with an embodiment of the present invention. Using such two-dimensional matrix ultrasound transducer 3 having a matrix of transducer elements 9 arranged in rows and columns it is possible to provide a field of view 10 in a shape of a truncated pyramid. Accordingly, the field of view is not restricted to a single plane but covers a three-dimensional space.

Information from within the field of view 10 can be displayed in many ways. As illustrated in FIG. 5a, a user may choose to view one or more planes 10' in the azimuth direction. Alternatively, as shown in FIG. 5b, image planes 10" in an elevation direction may be provided. Also any other orientation of image planes may be provided using a two-dimensional matrix ultrasound transducer.

Figure 6:
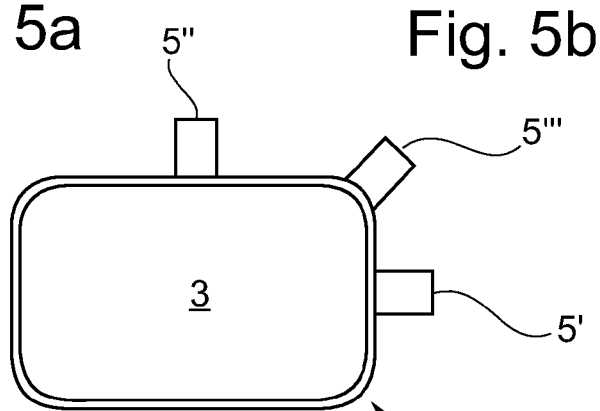
FIG. 6 schematically shows a top view on a multi-position biopsy guide system according to an embodiment of the present invention.
Figure 7:
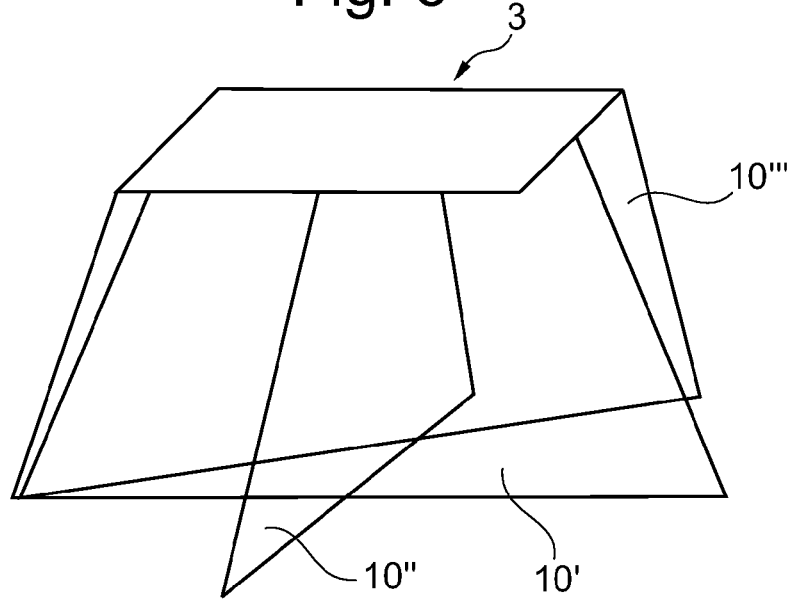
FIG. 7 schematically shows imaging planes corresponding to locations of biopsy needle guides of the embodiment of the present invention shown in FIG. 6.

As schematically indicated in the top view shown in FIG. 6, one or more biopsy needle guides 5', 5", 5'" may be provided at different locations around the two-dimensional matrix ultrasound transducer 3. With reference to FIG. 7, a first biopsy needle guide 5' in an azimuthal position may be aligned with an azimuth image plane 10'. A second biopsy needle guide 5'" arranged in a corner of the rectangular transducer face of the matrix transducer 3 may be aligned with a diagonal image plane 10'''. A third biopsy needle guide 5" arranged at an elevation position may be aligned with an elevation imaging plane 10".

Figure 8:
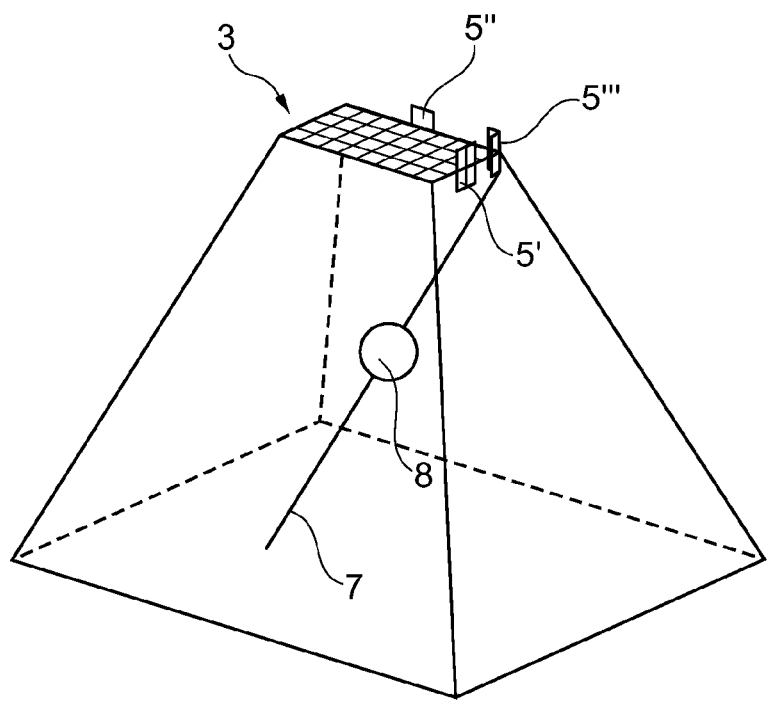
FIG. 8 shows a schematic representation of a 3D view of a lesion and a diagonal biopsy needle path for a multi-position biopsy guide system according to an embodiment of the present invention.
Figures 9A, 9B, 9C:
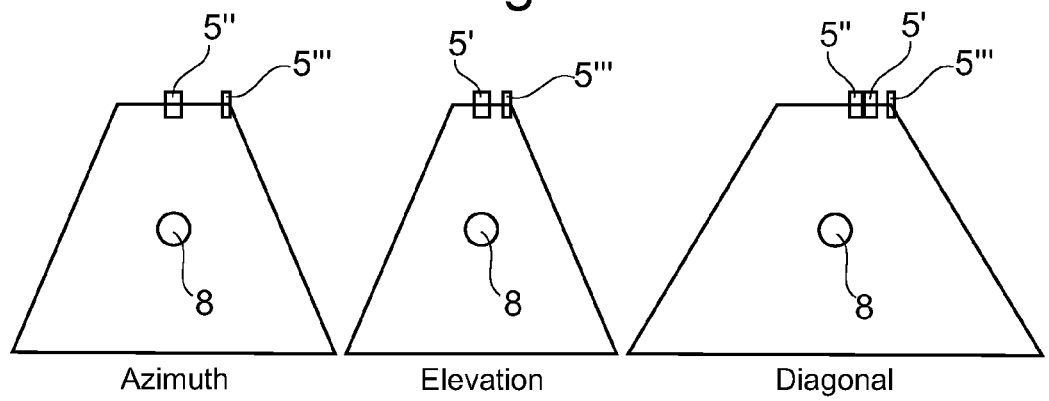
FIGS. 9a-9c show 2D cross-sections through the 3D volume of FIG. 8 in an azimuthal, elevational and diagonal direction.

FIG. 8 is a schematic representation of a three-dimensional field of view of a matrix transducer 3. Within the field of view is a lesion 8 to be biopsied. Around an edge of the transducer's 3 lens three small rectangle 5', 5", 5'" are illustrated to indicate potential locations for a biopsy needle guide with biopsy paths in the azimuth, elevation and diagonal planes, respectively. FIGS. 9a-9c show two-dimensional cross-sections through the three-dimensional volume shown in FIG. 8, and FIGS. 10a-10c show the same cross-sections with the addition of the biopsy path 7 appropriate to each plane.

With the multi-position biopsy guide system according to embodiments of the present invention, it is the ability of the 2D matrix transducer to view the other planes or the 3D view that make the multiple biopsy needle guide locations useful. Biopsy guidance in three dimensions may also provide better awareness of nearby structures and help to avoid mistakes during the procedure.

Figures 10A, 10B, 10C:
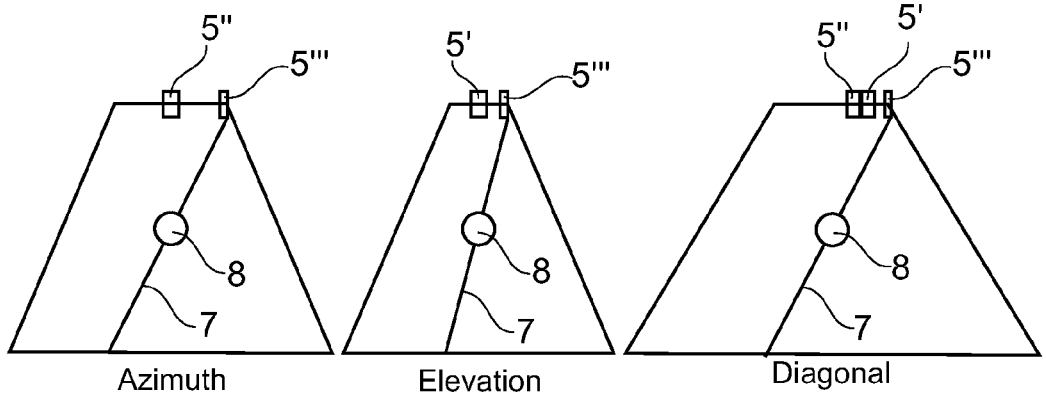
FIGS. 10a-10c show the cross-sections of FIGS. 9a-9c with the addition of a biopsy path appropriate to each plane.

Finally, it should be noted that the biopsy paths in the different imaging planes shown for example in FIGS. 10a-10c are all at different angles to pass through the lesion 8. Accordingly, it is useful to provide biopsy needle guides 5 which may be adapted to variable angles of the biopsy path.

It should be noted that the above-mentioned embodiments illustrate rather than limit the invention, and that those skilled in the art will be able to design many alternative embodiments without departing from the scope of the appended claims. The term "comprising" does not exclude other elements or steps and the term "a" or "an" does not exclude a plurality of elements. It should also be noted that reference signs in the claims should not be construed as limiting the scope of the claims. The invention may be implemented by means of hardware comprising several distinct elements, and/or by means of a suitably programmed processor. The mere fact that certain measures are recited in mutually different dependent claims does not indicate that a combination of these measures cannot be used to advantage.

LIST OF REFERENCE SIGNS 3 2D matrix ultrasound transducer
5 Biopsy needle guide

7 Biopsy path
8 Lesion
9 Transducer elements
10 Image plane
100 biopsy guide
103 Ultrasound transducer
104 Transducer face
105 Biopsy needle guide
106 Bracket
107 Biopsy path
108 Lesion
109 Transducer elements
110 Imaging plane

The invention claimed is:

1. A multiposition biopsy guide system, comprising:
a 2D matrix ultrasound transducer having transducer elements extending in an elevation direction and an azimuth direction;
a biopsy needle guide for guiding a biopsy needle along a biopsy path, the biopsy needle guide being adapted to couple to the transducer and controllably guide the biopsy needle along (1) three biopsy paths extending in the elevation direction, the azimuth direction, and a diagonal direction crossing both the elevation and azimuth directions and (2) at variable locations with respect to the 2D matrix ultrasound transducer, the locations comprising a first side of the 2D matrix ultrasound transducer at which the biopsy needle is aligned with an azimuth image plane of the transducer, a second side of the 2D matrix ultrasound transducer which is orthogonal to the first side and at which the biopsy needle is aligned with an elevation image plane of the transducer, and a third location at which the biopsy needle is aligned with a diagonal image plane of the transducer; and
a control device configured to generate a scan of a volume in front of the transducer and determine a location of the biopsy needle along at least one of the biopsy paths from the scan, and then align an imaging plane of the transducer with the biopsy needle according to the determined location of the biopsy needle from the scan and a user input or an indicator on the needle guide identifying the location of the biopsy needle.

2. The multiposition biopsy guide system according to claim 1, wherein the biopsy system is configured to locate, in real-time, positions of at least two biopsy needles inserted at different locations on the biopsy needle guide.

3. The multiposition biopsy guide system according to claim 1, wherein the biopsy needle guide comprises at least one mount for inserting the biopsy needle, wherein the mount can be moved along the azimuth or elevation dimensions of the ultrasound transducer.

4. The multiposition biopsy guide system according to claim 1, wherein the third location is located at an intersection of the first side and the second side.

5. The multiposition biopsy guide system according to claim 1, wherein the 2D matrix ultrasound transducer is adapted to acquire ultrasound images in an image plane, which image plane is controllably variable.

6. The multiposition biopsy guide system according to claim 5, wherein the multiposition biopsy guide system is adapted to mount the biopsy needle guide in variable locations with respect to the 2D matrix ultrasound transducer.

7. The multiposition biopsy guide system according to claim 6, wherein the multiposition biopsy guide system is adapted to determine the location of the biopsy needle guide with respect to the 2D matrix ultrasound transducer.

8. The multiposition biopsy guide system according to claim 6, wherein the multiposition biopsy guide system is adapted to acquire an ultrasound image in an image plane aligned with the biopsy path corresponding to the determined location of the biopsy needle guide.

9. The multiposition biopsy guide system according to claim 8, further comprising a second biopsy needle guide, wherein the multiposition biopsy guide system is adapted to acquire ultrasound images in respective image planes aligned with the biopsy paths of each of the biopsy needle guides.

10. The multiposition biopsy guide system according to claim 9, wherein the biopsy needle guide is adapted for guiding the biopsy needle along a biopsy path at controllably variable angles.

11. The multiposition biopsy guide system according to claim 10, wherein the biopsy needle guide is adapted for guiding different types of biopsy needles.

12. The multiposition biopsy guide system according to claim 11, wherein the 2D matrix ultrasound transducer is adapted to acquire 3D ultrasound images.

13. A method of controlling guidance of a biopsy needle along a biopsy path using the multiposition biopsy guide system according to claim 1, the method comprising:
selecting a biopsy needle guide with respect to the 2D matrix ultrasound transducer;
determining a location of the biopsy needle guide with respect to the 2D matrix ultrasound transducer such that the biopsy path will be aligned with a selected one of an azimuth image plane and an elevation image plane; and
generating a scan of a volume in front of the transducer;
determining a location of the biopsy needle along the biopsy path from the scan;
aligning an imaging plane of the transducer with the biopsy needle according to the determined location of the biopsy needle from the scan and a user input or an indicator on the needle guide identifying the location of the biopsy needle; and
acquiring an ultrasound image in an image plane aligned with a biopsy path corresponding to the determined location of the biopsy needle guide.

14. The method of claim 13, wherein the multiposition biopsy guide system further comprises separate biopsy needle guides, the method further comprising: guiding at least two biopsy needles using said separate biopsy needle guides; and visualizing each biopsy needle in respective corresponding imaging planes using the 2D matrix ultrasound transducer.

* * * * *